United States Patent [19]

Yip et al.

[11] Patent Number: 4,595,524

[45] Date of Patent: Jun. 17, 1986

[54] TWO COMPONENT STAIN COMPOSITION FOR PRODUCING A GIEMSA BLOOD STAIN EFFECT

[75] Inventors: Kin F. Yip; Frances F. Rhodes, both of Elkhart, Ind.

[73] Assignee: Miles Laboratories, Inc., Elkhart, Ind.

[21] Appl. No.: 594,182

[22] Filed: Mar. 28, 1984

[51] Int. Cl.$^4$ .................. G01N 31/00; G01N 1/00; B66D 3/04

[52] U.S. Cl. ..................... 252/408.1; 424/2; 424/3; 436/8; 436/17; 436/18

[58] Field of Search ............. 252/408.1; 424/3, 2; 436/8, 10, 17, 18; 8/501, 506, 618, 550, 602, 607, 608, 631, 94.1 R, 638, 644, 657

[56] References Cited

U.S. PATENT DOCUMENTS

| | | | |
|---|---|---|---|
| 2,992,971 | 7/1961 | Millman et al. | 424/3 |
| 3,546,334 | 12/1970 | Lerner et al. | 424/3 |
| 3,876,375 | 4/1975 | Maurukas | 252/408.1 |
| 4,299,726 | 11/1981 | Crews et al. | 436/10 |
| 4,302,355 | 11/1981 | Turner et al. | 436/10 |
| 4,382,075 | 5/1983 | Liqo et al. | 424/3 |
| 4,392,864 | 7/1983 | Helfrich et al. | 424/3 |

FOREIGN PATENT DOCUMENTS

| | | | |
|---|---|---|---|
| 2402204 | 9/1977 | France | 424/3 |

OTHER PUBLICATIONS

Lillie, *Histopathologic Technique and Practical Histochemistry*, 3rd ed., McGraw-Hill, New York (1965), pp. 584–589.

Lillie, et al., *Stain Technology*, 54 (1979), pp. 47–48.

*Primary Examiner*—Thomas Wallen
*Attorney, Agent, or Firm*—Jerome L. Jeffers

[57] ABSTRACT

Disclosed is a novel, 2 component Giemsa stain. The stain comprises a first component which is an aqueous solution of methylene blue, Azure B and a preservative and a second component which is an acetone/dimethyl formamide/water solvent system containing the sodium salt of eosin Y and a buffer. The Giemsa stain effect is obtained by first fixing a blood slide with methanol and then applying the freshly mixed first and second components of the stain. The slide is then rinsed and dried to prepare it for examination.

6 Claims, No Drawings

TWO COMPONENT STAIN COMPOSITION FOR PRODUCING A GIEMSA BLOOD STAIN EFFECT

BACKGROUND OF THE INVENTION

This invention relates to a blood staining system, and more particularly, to an effective, stable Giemsa stain suitable for use in automated blood slide staining devices. Romanowsky-type stains, e.g. Wright's solution and Giemsa's solution, comprise methylene blue and an eosin dye, normally in methanol solution, along with other allied dyes. Typical allied dyes include Azure A, Azure B and Azure C. While these stains are basically similar, Wright's solution differs from Giemsa solution in three respects:

a. Stain preparation—Wright stain solution is prepared with Wright stain powder (a mixture of eosin Y, methylene blue and azures) and methanol whereas Giemsa stain solution is prepared with Giemsa stain powder (a mixture of eosin Y, methylene blue and azures) and a mixture of methanol and glycerol.

b. Staining procedure—for Wright stain the specimens are fixed in methanol and then stained in a mixture of Wright stain solution and 3 to 5 parts of buffer; for Giemsa stain the specimens are fixed in methanol and then stained in a mixture of Giemsa stain solution and 20 to 50 parts of buffer.

c. Stain characteristics—a Giemsa stain gives more intense nuclear staining on all neutrophils than Wright stain. There is more distinct granulation in the neutrophil cytoplasm than is observed with the Wright stain because of the light overall cytoplasm staining. In addition, red blood cells appear more bluish when stained with a Giemsa stain rather than a Wright stain.

The original Giemsa stain which is described by Lillie in *Histopathologic Technique and Practical Histochemistry*, 3rd edition, McGraw-Hill, New York (1965), pages 584–589, was prepared with Giemsa powder (comprising eosin Y, methylene blue and azures) in glycerol. The procedure called for fixing the blood smear preparation with methanol and then staining it with a dilution of the Giemsa stain in buffer (the procedure called for dilution of 20 to 50 times with the buffer). This original procedure cannot be used with present day automated staining devices, such as those marketed under the Trademark Hema-Tek, because of the presence of glycerol which is not compatable with the stainer due to its high viscosity, the high dilution required and the long stain time.

The present invention involves a 2 component Giemsa stain which is well-suited for use in automated staining devices and a method of staining blood slides using this stain.

SUMMARY OF THE INVENTION

The present invention is a Giemsa blood stain which consists essentially of a freshly mixed solution of:

(a) a first component of an aqueous solution containing from 0.23 to 0.27% (w/v) of methylene blue together with 0.23 to 0.27% (w/v) Azure B and 0.018 to 0.022% (w/v) of a preservative;

(b) a second component which is made up of a solvent system of 12 to 13% (w/v) acetone, 6 to 6.5% (v/v) dimethyl formamide and the remainder water which solvent system contains 0.07 to 0.08% (w/v) of the sodium salt of eosin Y and a buffer which is capable of maintaining the pH of the second component at a range of from 6.75 to 7.0 wherein the volume ratio of the first component to the second component is 1:3 to 1:5.

DESCRIPTION OF THE INVENTION

A good performance with Giemsa stain characteristics was observed for slides stained with the formulation and procedures reported by Lillie, et al in *Stain Technology*, 54, page 47 (1979). This method involves staining the specimen with a mixture of Azure B, methylene blue, eosin Y, acetone and a phosphate buffer. However, several disadvantages were observed using this formulation and procedure which made them unsuitable for use in automated staining devices without extensive modification. These were: (1) the formulation consists of 5 solutions which need to be combined before the staining is initiated; (2) precipitation was observed in the stain very quickly; and (3) a long staining time (20-30 minutes) was required due to the decrease in the effective concentration of the stain as a result of precipitation. This work did help to establish the fact that a Giemsa characteristic stain can only be achieved by methanol fixation and staining with a stain solution containing a low concentration of organic solvents. Since the stain solution must necessarily contain a low concentration of organic solvents, high solubility of the stain in the solvent is required to keep precipitation at an acceptably low level.

In a typical automated stainer containing four stations, the first station is reserved for the absolute methanol used as fixative to preserve the morphology of the blood cells. Stations two and three can be used to deliver the 2 component stain to the slide with the fourth station being used for the rinse solution. Stations two and three can be arranged so as to have their solutions feed into a mixing coil so they are mixed thoroughly before reaching the slide but do not have sufficient contact with each other for precipitation to occur before mixing. This is necessary because, while the individual components are stable when stored individually, dye precipitation occurs quite rapidly once they are mixed.

Commercially available methylene blue and Azure B dyes are suitable for use in the present Giemsa stain. The concentrations of these dyes in their aqueous solution as set out above are critical because if the dye concentrations are too low, poor stain quality is obtained and the required characteristic of the specimen can not be observed. If the dye concentration is too high, the specimen is overstained thereby hindering its observation. Precipitation problems also occur with too concentrated a stain solution. In addition to the dyes, the first component should contain a preservative to act as an inhibitor of microbial growth. Suitable preservatives include phenol, sodium azide and a trialkyl benzyl ammonium chloride salt such as Barquat MS-100 marketed by Lonza, Inc. Too high a concentration of preservative results in poor stain quality whereas too low a concentration tends to limit the shelf life of the composition which accounts for the concentration limitations.

The second component contains the sodium salt of eosin Y (commercially available) together with a buffer system which is capable of maintaining its pH at a level from 6.75 to 7.0. A preferred buffer system is a combination of 0.28 to 0.3% monobasic potassium phosphate and 0.1 to 12% of a dibasic sodium phosphate all on a w/v basis based on the second component. This eosin Y (sodium salt) should be present in an amount of from 0.07 to 0.08% (w/v) of the second component. The narrow range of dye concentration is necessitated for the reasons described above with regard to the dyes in the first component. The buffer system is necessary because changes in the concentration of ingredients change the pH of the system. At a high pH, the specimen is stained more towards the bluish range whereas at a low pH it is stained more reddish. In addition, careful selection of the solvent system is critical to give the stain its characteristic Giemsa effect. The use of dimethyl formamide, acetone and water in the proportions indicated is essential to satisfactory performance because the Giemsa stain is highly soluble in this solvent system and will produce the desired Giemsa effect within the 1.5 to 2.5 minute time frame preferred for a stain to be used in automatic staining devices. Premixing of the first and second components in a volume ratio of 1:3 to 1:5 just before their application to the blood slide provides a stain which produces the Giemsa effect as evidenced by experienced slide readers.

After staining the slide, it should be rinsed with an aqueous solution of a buffer, a preservative and a surfactant in order to remove excess stain from the specimen. The buffer is further described in that it maintains the pH at a level of from 6.3 to 6.7. The phosphate buffer system described above is the buffer of choice. A surfactant is required as a component of the rinse solution to increase its effectiveness in removing excess stain from the specimen. Suitable surfactants include a nonionic surfactant such as Pluronic F86LF in a concentration of 0.08 to 0.12% (w/v).

The 2 component stain and the method of using it in blood slide staining are further illustrated by the following example:

EXAMPLE I

A Giemsa stain effect is achieved according to the present invention as follows:

A 4 component stain pack for use in an automated blood slide staining device having four pump stations is prepared. The stain pack comprises:

1. Fixative—anhydrous methanol to be fed to the first pump station.

2. Stain component I—a mixture of 0.25% methylene blue, 0.25% Azure B and 0.02% Barquat MS-100 in water solution to be fed to the second pump station.

3. Stain component II—a mixture of 0.073% eosin Y, 0.4% phosphate buffer system, 12.5% acetone and 6.25% dimethyl formamide in water solution to be fed to the third pump station.

4. Rinse solution—a mixture of buffer (0.087% phosphate system) preservative (0.01% Barquat MS-100) and surfactant (0.1% Pluronic F86LF) in water to be fed to the fourth pump station. Pluronic F86LF is a block copolymer of poly(oxyethylene and poly(oxypropylene) manufactured by BASF Wyandotte, Inc.

After the stainer was primed according to the manufacturer's specifications, it was loaded with blood specimen slides. Fixative was delivered to the slide to be stained and allowed to fix a particular specimen for 1 to 1.5 minutes whereupon the fixative was removed from the slide by draining. The slides were stained by mixing one part of stain component I and three to five parts of stain component II which were delivered to the slide surface immediately after mixing. The stain was allowed to interact with the blood specimen for 1.5 to 2.5 minutes and then drained from the slide. About 1 to 1.5 ml of the rinse solution was used to remove any residual stain or precipitation. The slide was then air-dried or dried by a stream of warm air to ready it for examination. Examination of the slide revealed intense nuclear staining on all neutrophil. The cytoplasm of the neutrophil were stained light; distinct granulation in the neutrophil cytoplasm was observed because of the light overall cytoplasm staining. Very good contrast between the nuclear and cytoplasm stainings were observed for the lymphocytes and monocytes. Good stainings are also observed for RBC, basophil and eosinophil.

Conventional Giemsa stain solutions are prepared with a mixture of methanol and glycerol. Because of the presence of a high concentration of viscous glycerol and the required long standing time, these solutions are not compatable with automated staining devices. Methanolic Wright-Giemsa stains which are prepared from commercial Giemsa stains show no distinct stain characteristic different from the methanolic Wright stain solution. Furthermore, because of the methanol content of these stains, severe deterioration of the stain components is observed. The Giemsa stain of the present invention gives the characteristic Giemsa effect that is distinct from the methanolic stain solutions. Distinct stain characteristics were observed in neutrophils, granulars, lymphocytes and monocyte cytoplasm stains. Because of the absence of methanol in the stain and the careful maintenance of pH, no deterioration of the stain components were found in the present stain.

What is claimed is:

1. A Giemsa blood stain which consists essentially of a freshly mixed solution of:
   (a) a first component of an aqueous solution containing from 0.23 to 0.27% (w/v) of methylene blue together with 0.23 to 0.27% (w/v) Azure B and 0.015 to 0.025% (w/v) of a preservative; and
   (b) a second component which is made up of a solvent system of 12 to 13% (w/v) acetone, 6 to 6.5% (v/v) dimethyl formamide and the remainder water which solvent system contains 0.07 to 0.08% (w/v) of the sodium salt of eosin Y and a buffer which is capable of maintaining the pH of the second component at a range of from 6.75 to 7.0 wherein the volume ratio of the first component to the second component is from 1:3 to 1:5.

2. The stain of claim 1 wherein the preservative is a benzyl ammonium chloride salt.

3. The stain of claim 1 wherein the buffer in the second component comprises 0.1 to 12% of a dibasic sodium phosphate and 0.28 to 0.3% of a monobasic potassium phosphate all on a w/v basis based on the second component.

4. A method of staining a blood smear to enhance microscopic examination thereof which method comprises the steps of:
   (a) contacting the blood smear with anhydrous methanol as fixative;
   (b) preparing a fresh Giemsa stain solution by mixing:
      i. a first component of an aqueous solution containing from 0.23 to 0.27% (w/v) of methylene blue together with 0.23 to 0.27% (w/v) Azure B and 0.015 to 0.025% (w/v) of a preservative; and
      ii. a second component which is made up of a solvent system of 12 to 13% (v/v) acetone, 6 to 6.5% (v/v) dimethyl formamide and the remainder water which solvent system contains 0.07 to 0.08% (w/v) of the sodium salt of eosin Y and a buffer system which is a combination of 0.28 to 0.3% (w/v) monobasic potassium phosphate and 0.1 to 0.12 dibasic sodium phosphate wherein the volume ratio of the first component to the second component is from 1:3 to 1:5.

(c) applying the fresh Giemsa stain solution to the blood smear; and (d) rinsing the blood smear with an aqueous solution of a buffer, a preservative and a surfactant.

5. The method of claim 4 wherein the preservative in the component is a benzyl ammonium chloride salt.

6. The method of claim 4 wherein the buffer in the second component comprises 0.1 to 12% of a dibasic sodium phosphate and 0.28 to 0.3% of a monobasic potassium phosphate all on a w/v basis based on the second component.

* * * * *